United States Patent [19]
Snead

[11] Patent Number: 4,927,362
[45] Date of Patent: May 22, 1990

[54] CONVERTIBLE BUCCAL TUBE

[75] Inventor: Wilford A. Snead, San Dimas, Calif.

[73] Assignee: Unitek Corporation, Monrovia, Calif.

[21] Appl. No.: 218,095

[22] Filed: Jul. 12, 1988

[51] Int. Cl.⁵ .............................................. A61C 3/00
[52] U.S. Cl. ........................................... 433/17; 433/8
[58] Field of Search ...................................... 433/17, 8

[56] References Cited
U.S. PATENT DOCUMENTS

| | | | |
|---|---|---|---|
| 3,391,461 | 7/1968 | Johnson | 433/17 |
| 3,838,514 | 10/1974 | Polak | 433/17 |
| 4,134,208 | 1/1979 | Pearlman | 433/8 |
| 4,498,867 | 2/1985 | Kesling | 433/17 |
| 4,781,582 | 11/1988 | Kesling | 433/17 |
| 4,820,151 | 4/1989 | Pospisil | 433/8 |

Primary Examiner—John J. Wilson
Attorney, Agent, or Firm—Donald M. Sell; Walter N. Kirn; James D. Christoff

[57] ABSTRACT

A sintered-metal convertible buccal tube for orthodontic use, and having a body with an integrally formed cover plate closing an outer side of an arch-wire slot. Lines of weakness are defined along opposite side edges of the cover plate so the plate can be sheared away from the body to open the slot at a later treatment phase.

12 Claims, 1 Drawing Sheet

CONVERTIBLE BUCCAL TUBE

BACKGROUND OF THE INVENTION

A convertible buccal tube is an appliance used by orthodontists during an early phase of treatment to correct malpositioned teeth. The tube is essentially an orthodontic bracket in which the buccal or cheek-facing side of the usual arch-wire slot is closed by a plate to form a tubular opening of typically rectangular cross section. The plate is brazed or spot-welded in place, and can be removed to convert the buccal tube to a conventional bracket during later stages of treatment.

Convertible buccal tubes have been in use for many years, and reference is made to U.S. Pat. No. 3,391,461 for further background information. Tubes of this type are normally used on younger children whose second molars have not yet grown in, but who have erupted first molars which serve as anchor teeth for an orthodontic arch wire. The covered arch-wire slot provides a terminal buccal-tube anchorage for the arch wire during early treatment.

When the second molars erupt, these newly emerged teeth are provided with banded brackets which take over the "anchor" function and receive the terminal ends of a longer arch wire. Prior to installation of the longer arch wire, the arch-wire cover plate on each first-molar tube is removed to convert the tube to a conventional molar bracket, and thus to enable normal edgewise treatment of the first molars. An improved tool to remove the cover plate is shown in my U.S. Pat. No. 4,669,979.

Known convertible buccal tubes are of two-piece construction (bracket and cover plate), and production expense is increased by the necessary welding, brazing or other attachment process for securing the plate to the appliance body. These known units also sometimes present cover-plate removal problems in that the plate may be awkward and difficult to sever from the underlying body.

SUMMARY OF THE INVENTION

The convertible buccal tube of this invention is an integrally molded, cast, sintered or machined product comprising an orthodontic bracket with a body defining an arch-wire slot which is covered on the buccal side by an integral cap or plate. The occlusal and gingival sides of the plate are joined to the bracket by integral portions of narrowed cross section forming potential fracture lines or frangible webs which break away in shear when the plate is removed.

Preferably, the bracket-body sidewalls defining the arch-wire slot have entrance surfaces which are outwardly inclined to widen the slot immediately beneath the frangible webs. In a presently preferred form, the outer or buccal surface of the junctions of the plate and body define longitudinally or mesiodistally extending notches which diminish the junction cross section above the widened entrance of the arch-wire slot.

DESCRIPTION OF THE PREFERRED EMBODIMENTS

Figure 1:
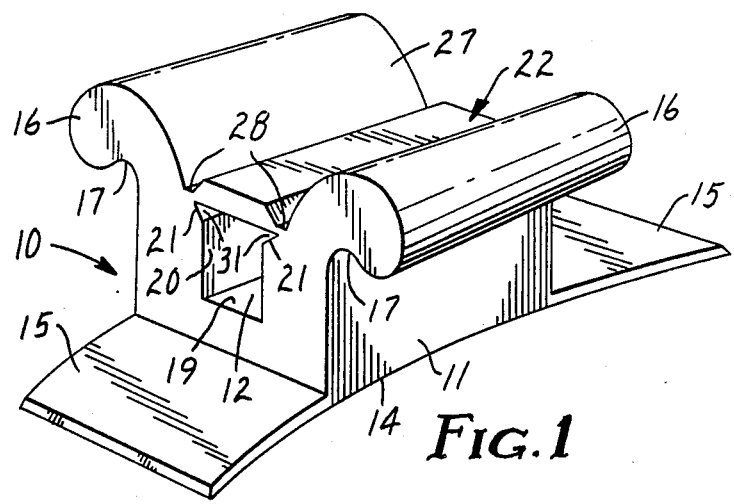
FIG. 1 is a pictorial view of a convertible buccal tube according to the invention.
Figure 2:
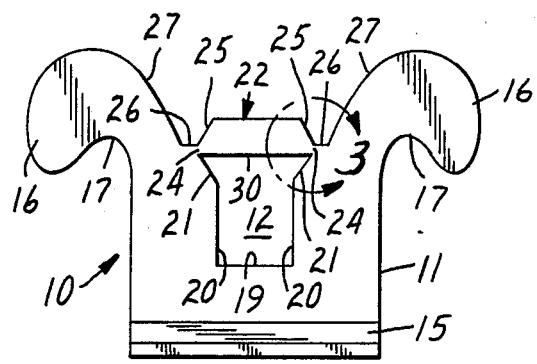
FIG. 2 is a side (mesiodistal) view of the buccal tube.

A convertible buccal tube 10 according to the invention is shown in FIGS. 1 and 2, and is preferably an integrally cast or sintered stainless-steel structure which is in some aspects similar to a conventional edgewise orthodontic bracket for a molar tooth. Tube 10 thus has a body 11 defining a mesiodistally extending slot 12 which is typically of rectangular cross section to receive an edgewise arch wire (not shown).

Body 11 has a base 14 which may include conventional mesiodistally extending welding flanges 15 for attachment to a molar tooth band (not shown). The body also defines a pair of tie wings 16 which curve occlusogingivally and lingually toward the base to define a pair of grooves or notches 17 for anchorage of a ligature wire or similar conventional retaining device.

Arch-wire slot 12 is defined by inner surfaces of the body which include a floor 19, and a pair of parallel and spaced-apart side surfaces 20. The outer or buccal end of each side surface diverges from the slot centerline to define an angled surface 21. The outer side of slot 12 is closed by a mesiodistally extending cover plate 22 which is integrally formed with body 11.

Figure 3:
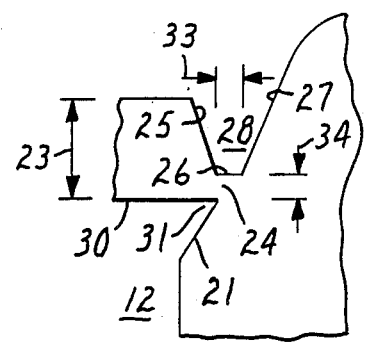
FIG. 3 is an enlarged view of portion 3—3 of FIG. 2.

The main body of cover plate 22 is relatively thick (dimension 23 in FIG. 3 is typically about 0.012 to 0.020 inch) for structural strength, but the opposite side edges of the plate are joined to body 11 by slender frangible webs 24 which extend along the slot 12 and which are of significantly reduced cross section as compared to the principal thickness of the plate. Cross-sectional slimming of webs 24 may be achieved by various geometries, and a presently preferred shape as shown in FIGS. 1–3 uses downwardly sloping (toward the base) side surfaces 25 on the cover plate. Surfaces 25 terminate at narrow flat surfaces 26 generally parallel to floor 19, and which extend outwardly to adjacent curved outer surfaces 27 of tie wings 16.

Surfaces 25, 26 and 27 define shear notches 28 (FIG. 3) along the full mesiodistal length of the outer or buccal side edges of the cover plate. Similarly, the junction of inner surface 30 of the plate and angled surfaces 21 of the arch-wire slot define a second pair of inner shear notches 31. These shear notches define therebetween frangible webs 24 which are intentionally structurally weakened to enable controlled separation of the cover plate from the body along preferential and predetermined lines of separation.

In a typical configuration, narrow flat surfaces 26 of shear notches 28 have a width (dimension 33 in FIG. 3) of about 0.006 to 0.010 inch, but this width is not considered critical, and is primarily for molding convenience. If desired, surfaces 26 can be eliminated to make the shear notches V-shaped in cross section. The thickness (dimension 34 in FIG. 3) of frangible webs 24 is nominally in the range of 0.003 to 0.004 inch, and this dimension may vary somewhat depending on the metal or other material selected to make the buccal tube.

In use, the buccal tube 10 is typically secured to a tooth band which is in turn cemented to a first molar tooth. Direct-bonding techniques may also be used, though banded attachment is normally preferred on these posterior teeth. A terminal end of a conventional arch wire is then fitted into the tube for early-stage orthodontic treatment. After the patient's second molars erupt sufficiently, these teeth are banded with buccal tubes to serve as the terminal anchoring teeth in the dental arch. The initial arch wire is removed, and the cover plates are removed from buccal tubes 10 on the first molars to convert these tubes to edgewise brackets with buccally open arch-wire slots. An older technique for cover-plate removal involves use of a prying tool inserted in the arch-wire slot and manipulated to shear the plate away from the underlying body. As mentioned above, an improved cap or cover-plate shearing tool is described in U.S. Pat. No. 4,669,979, and, for brevity, the disclosure of that patent is incorporated herein by reference.

The placement of shear notches 28 and 31 provide a number of advantages for buccal tube 10:

a. Shearing force required to separate the cover plate from the body is predictable and controlled by the geometry of frangible webs 24. As disclosed, the cover plate will separate from the body with application of a shearing force in the range of about 12 to 20 pounds (16 pounds being the preferred value), while still providing adequate structural integrity of the tube during first-stage treatment.

b. The cover plate severs cleanly from the body along the shear notches, and with minimum risk that only one side of the plate will separate. The thick main body of the cover plate prevents unwanted separation of the plate at positions other than along the shear notches, and helps to insure unitary removal of the plate without mere bending along one of the webs.

c. Any roughness or burrs remaining on body 11 along the line of shear webs 24 is recessed within the body between and beneath the buccal tips of the tie wings to prevent irritation of adjacent cheek tissue.

d. Outwardly sloping surfaces 21 at the outer end of the arch-wire slot position webs 24 to be spaced slightly above and below (i.e., occlusogingivally) side surfaces 20 which make a close fit over the arch wire used in second-stage treatment after the cover plate is removed. Any roughness or burrs remaining on body 11 along the lines of webs 24 will thus not intrude into the opened entrance of the slot, and will not interfere with seating of the arch wire.

Figure 4:
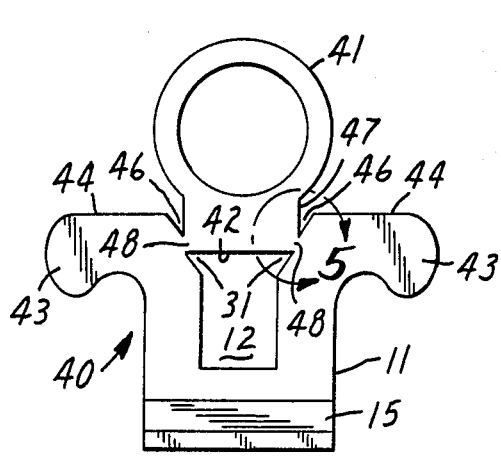
FIG. 4 is a side view of a second embodiment of the convertible buccal tube of this invention.
Figure 5:
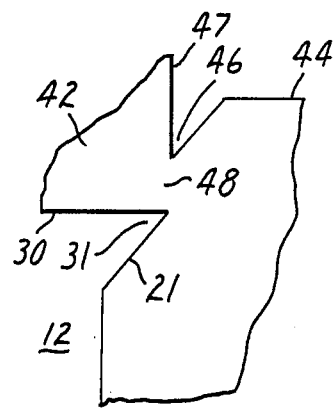
FIG. 5 is an enlarged view of portion 5—5 of FIG. 4.

The concept of this invention can be used in orthodontic buccal tubes of many different styles, and a typical alternative embodiment of a buccal tube 40 is shown in FIGS. 4 and 5. Many of the structural features of this buccal tube are similar to those of tube 10, and are designated with the same numbers. The primary difference is in the addition of an auxiliary tube 41 integrally formed on a cover plate 42 which is part of the unitary structure of tube 10. The auxiliary tube is useful in the early stages of some orthodontic treatment programs, and can be removed with the cover plate after the second molars become available as anchor teeth.

In tube 40, tie wings 43 have generally flat outer or buccal surfaces 44. Outer shear notches 46 are formed in surfaces 44 on opposite sides of a base 47 of auxiliary tube 41. FIG. 5 shows the detail of frangible webs 48 which are defined between inner and outer shear notches 31 and 46.

Many other variations are practical and useful, and the invention has intentionally been disclosed in the context of a very simple edgewise orthodontic system. The inventive concept is equally effective in more complex systems where, for example, one or multiple auxiliary tubes of varying cross section may be permanently secured to the buccal-tube body to remain in place after the cover plate is removed. Hooks may be positioned on the body or cover plate, and the base and arch-wire slot may also be angulated to provide torque, tip, and in-out compensation in conventional straight-wire applications.

An important feature of the invention is the production economy achieved by making the cover plate an integral part of the buccal-tube body. This construction can be achieved in a cast or machined structure, and a presently preferred technique is sintering, wherein the entire buccal tube is initially formed as a pressed "green" preform of metal powder, and then heated to sintering temperature to yield the final product. The sintering technique has been used to produce experimental buccal tubes from stainless-steel powder (Type 316L is satisfactory), and the cover plates on these tubes can be sheared cleanly from the tube bodies with application of predicted shearing force.

There has been described an orthodontic appliance having an arch-wire slot which is covered on its buccal end by a plate secured to the appliance body by frangible webs of narrow cross section. This construction enables opening of the slot for subsequent use of the appliance as an orthodontic bracket when an initial stage of treatment is complete. The appliance has been described in terms of conventional placement on the outer or buccal face of a molar tooth, but this terminology is not intended to be restrictive with respect to possible utility of the appliance in lingual treatment programs.

What is claimed is:

1. An integral, convertible buccal tube made of sintered metal for mounting on a molar tooth in an orthodontic treatment program, comprising:
   a base configured for fitting on a tooth;
   a body extending integrally from the base, and defining an elongated arch-wire slot; and
   a cover plate extending across and closing a buccal side of the arch-wire slot, the plate being integrally joined to the body adjacent opposite sides of the slot by elongated, frangible webs extending along the length of the slot, the webs being of small cross section as compared to the cover plate buccal-lingual thickness, whereby the plate can be sheared from the body along both of the webs to open the slot.

2. The tube defined in claim 1 wherein the arch-wire slot includes a pair of parallel and spaced-apart side surfaces, and wherein the body includes diverging, outwardly sloping surfaces connected to the arch-wire side surfaces.

3. An integral, convertible buccal tube made of sintered metal for mounting on a molar tooth in an orthodontic treatment program, comprising:
   a base configured for fitting on a tooth;
   a body extending integrally from the base, and defining an elongated arch-wire slot; and
   a cover plate extending across and closing a buccal side of the arch-wire slot, the plate being secured to the body adjacent opposite sides of the slot by elongated frangible webs extending along the length of the slot, the webs being of small cross section as compared to the cover plate buccal-lingual thickness, whereby the plate can be sheared from the body along both of the webs to open the slot, wherein the arch-wire slot is generally rectangular and is enlarged in width at the buccal side beneath the cover plate to position the webs to be spaced apart along an occlusogingival axis from sidewalls of the slot, and wherein the cover plate and body are integrally joined.

4. The tube defined in claim 3 wherein the cover plate has side edges forming mesiodistally extending notches which reduce the cross section of the webs.

5. The tube defined in claim 3 wherein the enlarged buccal side of the slot and an undersurface of the cover plate define therebetween mesiodistally extending notches which reduce the cross section of the webs.

6. The tube defined in claim 3 wherein the webs have a cross-sectional thickness in the range of about 0.003 to 0.004 inch.

7. The tube defined in claim 6 wherein the cover plate and base are integrally formed of sintered metal.

8. An integral, convertible buccal tube made of sintered metal for mounting on a molar tooth in an orthodontic treatment program, comprising:
 a body having an attachment base, the body defining a mesiodistally extending arch-wire slot therethrough; and
 a cover plate integrally joined to the body and extending across the slot, the plate having an inner surface with a pair of spaced apart and oppositely extending inner notches to form weakened elongated frangible webs extending along the length of the slot between the body and side edges of the plate, whereby the plate can be sheared from the body along both of the webs to open the slot.

9. An integral, convertible buccal tube made of sintered metal for mounting on a molar tooth in an orthodontic treatment program, comprising:
 a body having an attachment base, the body defining a mesiodistally extending arch-wire slot therethrough; and
 a cover plate secured to the body and extending across the slot, the plate having an inner surface with a pair of spaced apart and oppositely extending inner notches to form weakened elongated frangible webs between the body and side edges of the plate, whereby the plate can be sheared from the body along both of the webs to open the slot, wherein the arch-wire slot is in part formed by a floor surface and a pair of parallel spaced-apart sidewall surfaces extending generally perpendicularly to the floor surface, the frangible webs being spaced from and on opposite sides of the sidewall surfaces, and wherein the cover plate and body are integrally formed.

10. The tube defined in claim 9 wherein the cover plate has an outer buccal surface defining a pair of spaced-apart mesiodistally extending outer notches positioned adjacent the inner notches, the inner and outer notches defining therebetween the frangible webs.

11. The tube defined in claim 10 wherein the body cover plate and webs are integrally formed of sintered stainless steel.

12. The tube defined in claim 11 wherein the webs have a thickness of about 0.003 to 0.004 inch, and the cover plate between the webs is substantially thicker and stronger than the webs.

* * * * *